(12) United States Patent
Ozawa et al.

(10) Patent No.: US 8,553,077 B2
(45) Date of Patent: Oct. 8, 2013

(54) ENDOSCOPE SYSTEM

(75) Inventors: Satoshi Ozawa, Kanagawa (JP); Azuchi Endo, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 442 days.

(21) Appl. No.: 12/890,153

(22) Filed: Sep. 24, 2010

(65) Prior Publication Data
US 2011/0069164 A1 Mar. 24, 2011

(30) Foreign Application Priority Data

Sep. 24, 2009 (JP) ................................ P2009-219243
May 25, 2010 (JP) ................................ P2010-119747

(51) Int. Cl.
*A61B 1/04* (2006.01)
*A61B 6/00* (2006.01)
*A61B 1/06* (2006.01)

(52) U.S. Cl.
USPC ............................ 348/68; 600/178; 600/473

(58) Field of Classification Search
USPC .......................................................... 348/68
See application file for complete search history.

(56) References Cited

U.S. PATENT DOCUMENTS

| | | | |
|---|---|---|---|
| 4,827,908 A | | 5/1989 | Matsuo |
| 5,807,261 A | * | 9/1998 | Benaron et al. ............... 600/473 |
| 6,778,208 B2 | * | 8/2004 | Takeshige et al. .............. 348/65 |
| 2007/0149857 A1 | * | 6/2007 | Yabe et al. ..................... 600/180 |
| 2009/0062617 A1 | * | 3/2009 | Mizuyoshi .................... 600/178 |

FOREIGN PATENT DOCUMENTS

| | | |
|---|---|---|
| EP | 1 650 982 A1 | 4/2006 |
| EP | 2 030 559 A1 | 3/2009 |
| JP | 2000-342533 A | 12/2000 |

OTHER PUBLICATIONS

European Search Report dated Dec. 23, 2010.

\* cited by examiner

*Primary Examiner* — Sath V Perungavoor
*Assistant Examiner* — Howard D Brown, Jr.
(74) *Attorney, Agent, or Firm* — McGinn IP Law Group, PLLC

(57) ABSTRACT

An endoscope system includes an endoscope and a control device. The endoscope includes an illumination optical system with a fluorescent body formed in an optical path and an imaging optical system with an imaging element outputting an imaging signal of an optical image. The control device includes a light source unit which supplies an excitation light to the illumination optical system so as to emit light from the fluorescent body and an image processing section which corrects the imaging signal output from the imaging element. The image processing section includes: an illumination light spectrum calculating unit, a chromaticity correction table creating unit and an image correcting unit.

14 Claims, 9 Drawing Sheets

ENDOSCOPE SYSTEM

The present application claims priority from Japanese Patent Application No. 2009-219243 filed on Sep. 24, 2009 and Japanese Patent Application No. 2010-119747 filed on May 25, 2010, the entire content of which is incorporated herein by reference.

BACKGROUND OF INVENTION

1. Field of the Invention

The present invention relates to an endoscope system.

2. Description of the Related Art

For example, JP-A-2000-342533 discloses an endoscope system including an endoscope which has an imaging element emitting illumination light from a front end of an endoscope insertion unit and capturing an image of an observation area, and a control device which supplies the illumination light to the endoscope while being connected to the endoscope, and performs a calculation process on an imaging signal from the imaging element. In addition, recently, a technology of using a combination of a fluorescent body and laser light as the illumination light of the endoscope has been put to practical use. In the case of the endoscope system using the illumination light formed by the fluorescent body and the laser light, the fluorescent body is disposed in the front end of the endoscope insertion unit, and the laser light is supplied to the fluorescent body via a thin optical fiber cable, which is an advantage in that the endoscope insertion unit is thin.

In such an endoscope system, in order to accurately examine an affected portion, a chromaticity adjustment process is performed by correcting the chromaticity of a captured image to be the correct chromaticity on the basis of a predetermined chromaticity correcting table. However, there is an individual difference in the optical characteristics of each endoscope and the optical characteristics of a control device to which the endoscope is connected. For this reason, even when the uniform correction of the image signal output from the endoscope is attempted by the control device, it is difficult to perform the correction with correct chromaticity at all times. Particularly, in the case of the illumination device obtained by combining the fluorescent body with the laser light source, since the tone of the final observation image is determined by the delicate relationship of the difference in the light emission characteristics caused by the individual difference of the fluorescent body or the difference in the light emission wavelength caused by the individual difference of the illumination light source, when the endoscope connected to the control device is exchanged with another one, the tone of the captured image may be different for each endoscope.

FIG. 12 shows a distribution of a variation in the illumination light of the endoscope caused by the individual differences of chromaticities (X, Y) of the light sources. When the laser light source is used, since the laser light emitting element has a variation in the light emission wavelength of about ±5 nm, a variation in the chromaticity caused by the individual differences of the light sources (for example, excitation light sources of 440 nm and 445 nm) is about 0.02 in the chromaticities X and Y. When a variation in the characteristics of the illumination light is small, the variation can be adjusted by a white balance function provided in a control device. However, when a variation caused by the individual differences is large, and is out of an adjustable range, the correct tone cannot be realized even when the white balance adjustment is performed. For this reason, the chromaticity of the illumination light determines the color quality of the observation image.

SUMMARY OF INVENTION

An object of the invention is to provide an endoscope system that uses an illumination light formed by a combination of a fluorescent body and a light source and is capable of correcting an observation image to have the same tone at all times even when there are individual differences in the optical characteristics of an endoscope and a control device attached to the endoscope.

According to an aspect of the invention, an endoscope system includes: an endoscope that includes an illumination optical system with a fluorescent body formed in an optical path and an imaging optical system with an imaging element outputting an imaging signal of an optical image; and a control device that includes a light source unit which supplies an excitation light to the illumination optical system so as to emit light from the fluorescent body and an image processing section which corrects the imaging signal output from the imaging element, wherein the image processing section includes: an illumination light spectrum calculating unit for calculating an illumination light spectrum obtained by the illumination optical system based on individual information of light emission characteristics of the fluorescent body provided in the endoscope connected to the control device and individual information of light emission characteristics of the light source unit; a chromaticity correction table creating unit for creating a chromaticity correction table to correct chromaticity information of the imaging signal in accordance with the illumination light spectrum; and an image correcting unit for correcting the imaging signal output from the imaging element by referring the created chromaticity correction table.

According to the invention, in the endoscope system that uses the illumination light formed by a combination of the fluorescent body and the light source, even when there are individual differences in the optical characteristics of the endoscope and the control device to which the endoscope is connected, the observation image may be corrected to have the same tone at all times in consideration of the difference in the light emission characteristics of the fluorescent body or the light source.

DESCRIPTION OF EXEMPLARY EMBODIMENTS

Hereinafter, an embodiment of the invention will be described with reference to the accompanying drawings.

Figure 1:
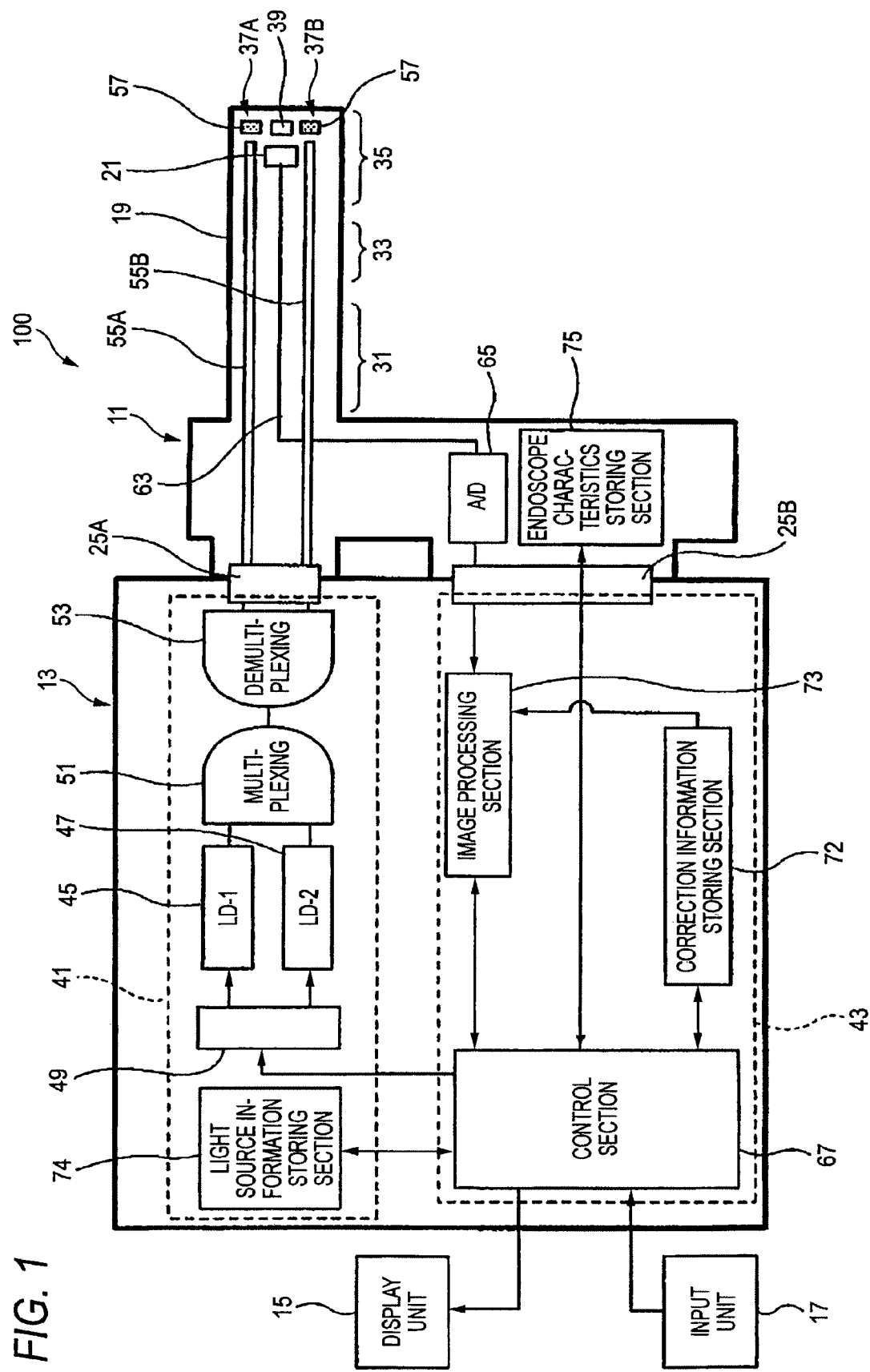
FIG. 1 is a diagram illustrating an embodiment of the invention, and is a block diagram illustrating an endoscope system.
Figure 2:
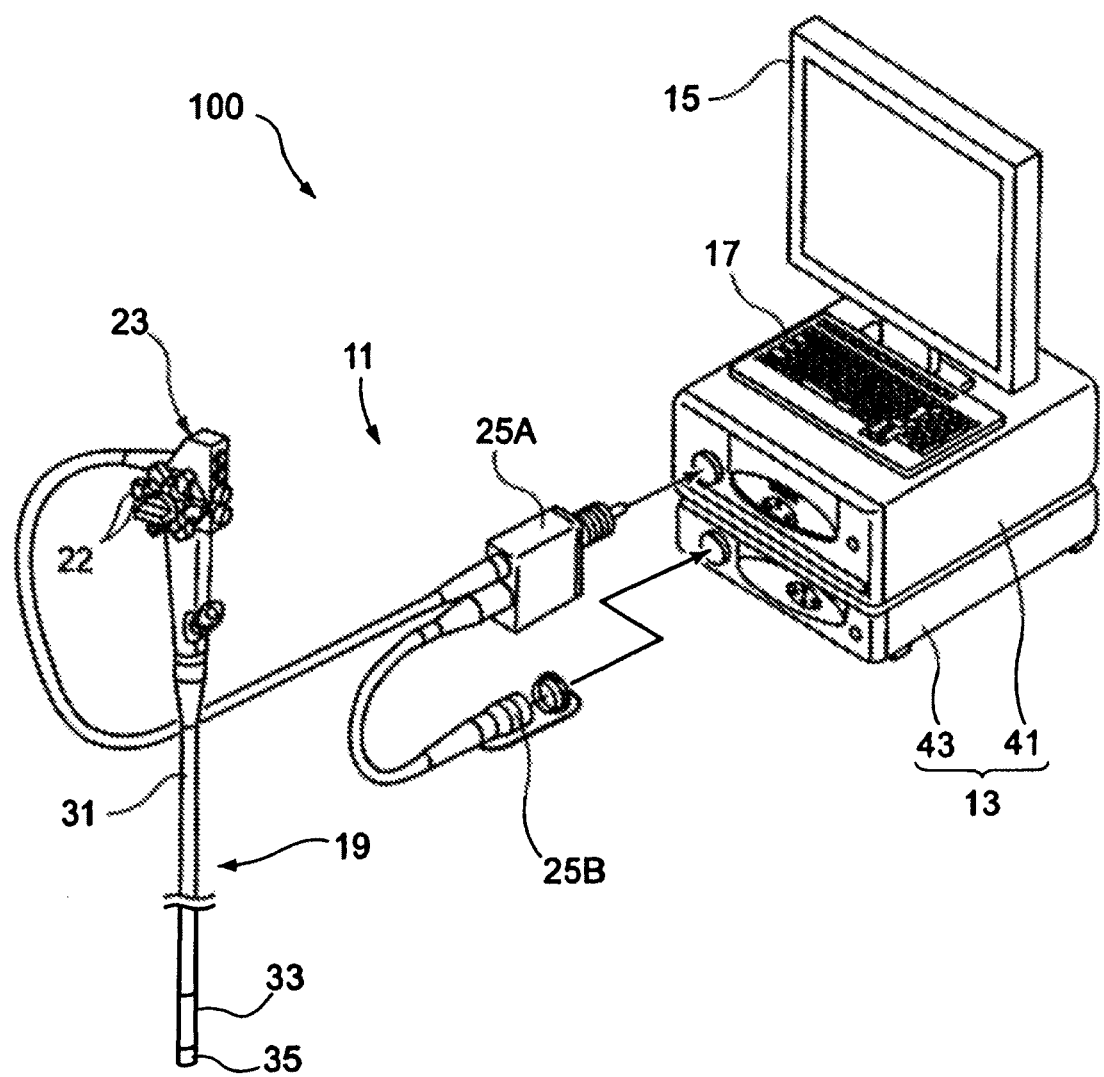
FIG. 2 is an external view of an example of the endoscope system shown in FIG. 1.

FIG. 1 is a diagram illustrating an embodiment of the invention, and is a conceptual block diagram illustrating an endoscope system. FIG. 2 is an external view of an example of the endoscope system shown in FIG. 1.

As shown in FIGS. 1 and 2, an endoscope system 100 includes an endoscope 11, and a control device 13 to which the endoscope 11 is connected. The control device 13 is connected to a display unit 15 which displays image information or the like, and an input unit 17 which receives an input operation. The endoscope 11 is an electronic endoscope which includes an illumination optical system emitting an illumination light from a front end of an endoscope insertion unit 19 and an imaging optical system including an imaging element 21 (refer to FIG. 1) configured to capture an image of an observation area.

In addition, the endoscope 11 includes the endoscope insertion unit 19 which is inserted into a test object, an operation unit 23 (refer to FIG. 2) which is used for an operation of curving the front end of the endoscope insertion unit 19 or an observation operation, and connectors 25A and 25B which are used to attachably/detachably connect the endoscope 11 to the control device 13. In addition, although not shown in the drawings, various channels such as a forceps channel used for inserting a tissue pickup treatment tool or the like therethrough or an air/water feeding channel are installed inside the operation unit 23 and the endoscope insertion unit 19.

The endoscope insertion unit 19 includes a flexible portion 31 with flexibility, a curved portion 33, and a front end portion (hereinafter, referred to as an endoscope front end portion) 35. As shown in FIG. 1, the endoscope front end portion 35 is provided with illumination ports 37A and 37B which are used to emit a light to the observation area, and an imaging element 21 such as a CCD (Charged Coupled Device) image sensor or a CMOS (Complementary Metal-Oxide Semiconductor) image sensor which is used to acquire image information of the observation area. The light receiving surface of the imaging element 21 is provided with an object lens unit 39.

The curved portion 33 is provided between the flexible portion 31 and the front end portion 35, and is adapted to be curved by a rotation operation of an angle knob 22 disposed in the operation unit 23. The curved portion 33 may be curved to an arbitrary direction and an arbitrary angle in accordance with a portion of the test object examined by the endoscope 11. The observation direction of the illumination ports 37A and 37B and the imaging element 21 of the endoscope front end portion 35 may be directed to a desired observation portion in the test object. In addition, although not shown in the drawings, the illumination ports 37A and 37B of the endoscope insertion unit 19 are provided with a cover glass or a lens.

The control device 13 includes a light source device 41 which generates an illumination light supplied to the illumination ports 37A and 37B of the endoscope front end portion 35, and a processor 43 which performs an image process on an image signal generated from the imaging element 21, and is connected to the endoscope 11 via the connectors 25A and 25B. In addition, the processor 43 is connected to the display unit 15 and the input unit 17 which are described above. The processor 43 performs an image process on an imaging signal transmitted from the endoscope 11 on the basis of the command from the operation unit 23 of the endoscope 11 or the input unit 17 thereof, and generates and supplies a display image to the display unit 15.

In addition, a plurality of the endoscopes 11 is provided in advance, and one of the plurality of the endoscopes 11 connected to the control device 13 may be arbitrarily exchanged.

As shown in FIG. 1, the light source device 41 includes a violet laser light source (LD-1) 45 and a blue laser light source (LD-2) 47 as light sources. Specifically, the blue laser light source 47 is a laser diode that emits a blue laser light having a central wavelength of 445 nm, and the violet laser light source 45 is a laser diode that emits a violet laser light having a central wavelength of 405 nm.

As the violet laser light source 45 and the blue laser light source 47, a broad area type InGaN-based laser diode may be used, and also an InGaNAs-based laser diode or a GaNAs-based laser diode may be used. In addition, a light emitter such as a light emitting diode may be used as the light source.

The lights emitted from the semiconductor light emitting elements of the light sources 45 and 47 are individually controlled by the light source control section 49, and the light amount ratio between the light emitted from the violet laser light source 45 and the light emitted from the blue laser light source 47 is set to be arbitrarily changed.

The laser lights emitted from the light sources 45 and 47 are input to an optical fiber by a condensing lens (not shown), and are propagated to the connector 25A via a combiner 51 as a multiplexer and a coupler 53 as a demultiplexer. In addition, the invention is not limited thereto, and a configuration may be adopted in which the laser lights emitted from the light sources 45 and 47 are directly propagated to the connector 25A without using the combiner 51 and the coupler 53.

The laser light formed by multiplexing the blue laser light having a central wavelength of 445 nm and the violet laser light having a central wavelength of 405 nm supplied to the connector 25A is propagated to the endoscope front end portion 35 of the endoscope 11 via two optical fibers 55A and 55B so as to be used as two channels of lights.

As shown in FIG. 1, a fluorescent body 57 is disposed at the positions facing the light emitting ends of the optical fibers 55A and 55B of the endoscope front end portion 35. The fluorescent body 57 serves as a wavelength converting member. That is, the blue laser lights supplied from the blue laser light source 47 via the optical fibers 55A and 55B excite the fluorescent bodies 57 to emit fluorescent lights. In addition, a part of the blue laser light is directly transmitted through the fluorescent body 57. On the other hand, the violet laser light supplied from the violet laser light source 45 is transmitted through the fluorescent body 57 without the excitation thereof, and is used as a narrowband wavelength illumination light.

Each of the optical fibers 55A and 55B is a multi-mode fiber. As an example, a thin fiber cable may be used which has a core diameter of 105 μm, a cladding diameter of 125 μm, and a diameter of φ0.3 to 0.5 mm including a protection layer as an outer cover.

The fluorescent body 57 includes a plurality of types of fluorescent bodies which absorb a part of energy of the blue laser light and are excited to emit light of green to yellow. As a specific example of the fluorescent body 57, for example, a YAG-based fluorescent body or a fluorescent body containing BAM ($BaMgAl_{10}O_{17}$)) or the like may be used. Accordingly, white (color similar to white) illumination light is emitted from the illumination ports 37A and 37B of the endoscope front end portion 35 as the result of synthesizing green to yellow excitation light as excitation light with the blue laser light not absorbed by and passing through the fluorescent body 57. Like the example of the configuration, when the semiconductor light emitting element is used as an excitation light source, it is possible to obtain white light having high light emission efficiency and high intensity. Also, it is possible to easily control the intensity of the white light.

The fluorescent body 57 may prevent an occurrence of flickering when performing a video display or overlapping of noise as a barrier in the imaging operation due to a speckle generated by the coherence of the laser light. In addition, in the fluorescent body 57, in consideration of a difference in the refractive index between the fluorescent material forming the fluorescent body and a fixing/solidifying resin as a filling agent, it is desirable that the particles of the filling agents and the fluorescent material are formed of a material having large scattering and small absorption with respect to the infrared light. Accordingly, since the scattering effect is improved without reducing the light intensity with respect to the light of a red or an infrared region, and an optical path changing means such as a concave lens is not needed, it is possible to reduce the optical loss.

Figure 3:
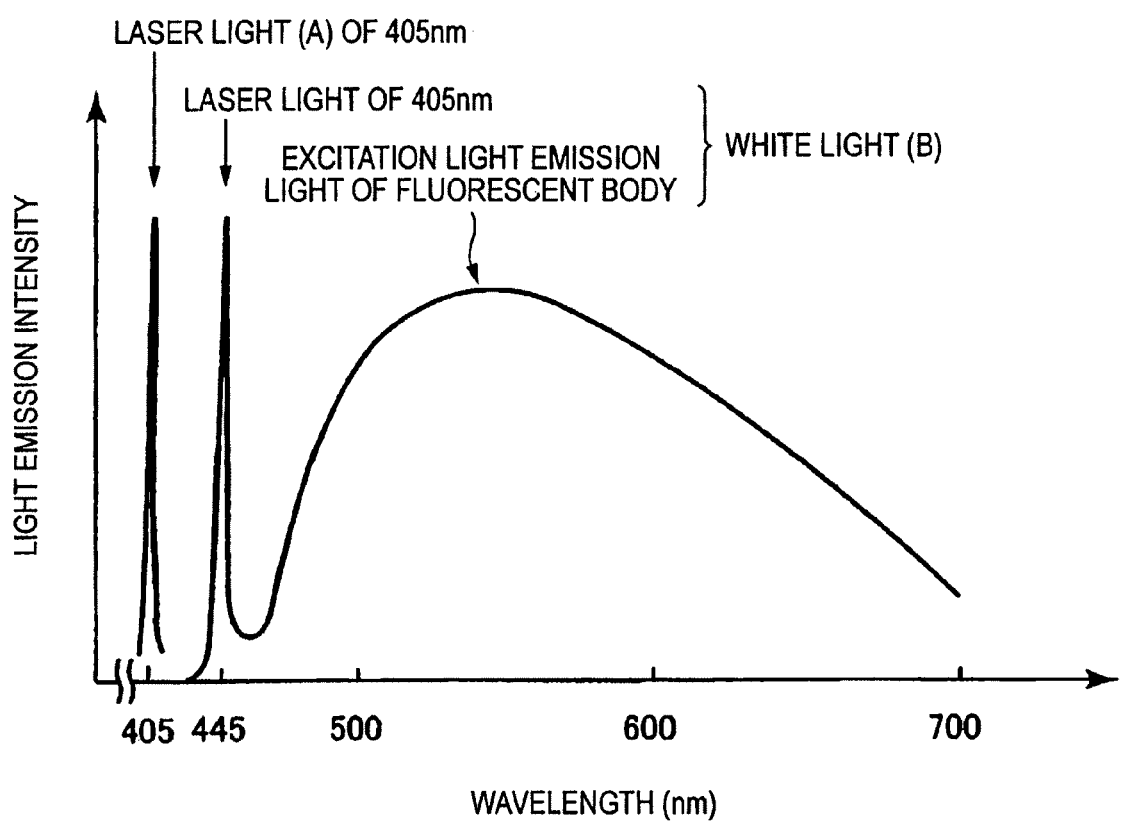
FIG. 3 is a graph showing a light emission spectrum of a violet laser light emitted from a violet laser light source, a blue laser light emitted from a blue laser light source, and the blue laser light having a wavelength converted by a fluorescent body.

FIG. 3 is a graph showing a light emission spectrum of the violet laser light emitted from the violet laser light source 45, the blue laser light emitted from the blue laser light source 47, and the blue laser light having a wavelength converted by the fluorescent body. The violet laser light is depicted by the bright line (profile A) having a central wavelength of 405 nm, and the blue laser light is depicted by the bright line having a central wavelength of 445 nm. The excitation light emitted from the fluorescent body 57 by the blue laser light has a spectral intensity distribution in which the light emission intensity substantially increases in the wavelength bandwidth of 450 nm to 700 nm. The above-described white light is formed by the profile B of the excitation light and the blue laser light.

Here, the white light mentioned in the specification specifically includes not only all wavelength components of the visible light, but also for example, R, G, B, and the like of the light of the specific wavelength. For example, the light including the wavelength component from green to red or the light including the wavelength component from blue to green is included in the white light in a broad sense.

In the endoscope system 100, since the light intensities of the profiles A and B are controlled by the light source control section 49 so as to be relatively increased or decreased, it is possible to obtain the illumination light having different characteristics in accordance with a combination ratio of the profiles A and B.

Returning to FIG. 1, the description thereof is continued. As described above, the illumination light formed by the white light of the excitation light emitted from the fluorescent body 57 and the blue laser light and the narrow bandwidth light formed by the violet laser light are emitted from the front end portion 35 of the endoscope 11 to the observation area of the test object. Then, the image of the observation area illuminated by the illumination light is formed and captured on the light receiving surface of the imaging element 21 by the use of the object lens unit 39.

The image signal of the captured image output from the imaging element 21 after the imaging operation thereof is transmitted to an A/D converter 65 via a scope cable 63 and is converted into a digital signal. Then, the digital signal is input to the processor 43 via the connector 25B.

The processor 43 includes a control section 67 which controls the light source device 41, an image processing section 73 which is connected to the control section 67 and is described later in detail, and a correction information storing section 72. Information such as a chromaticity correction table necessary for a correction process of matching the imaging signal to the correct chromaticity is created in advance, and is stored in the correction information storing section 72.

The imaging signal output from the A/D converter 65 is input to the image processing section 73. The image processing section 73 performs an appropriate image process by converting the input digital image signal into the image data, and creates the desired output image information.

Figure 4:
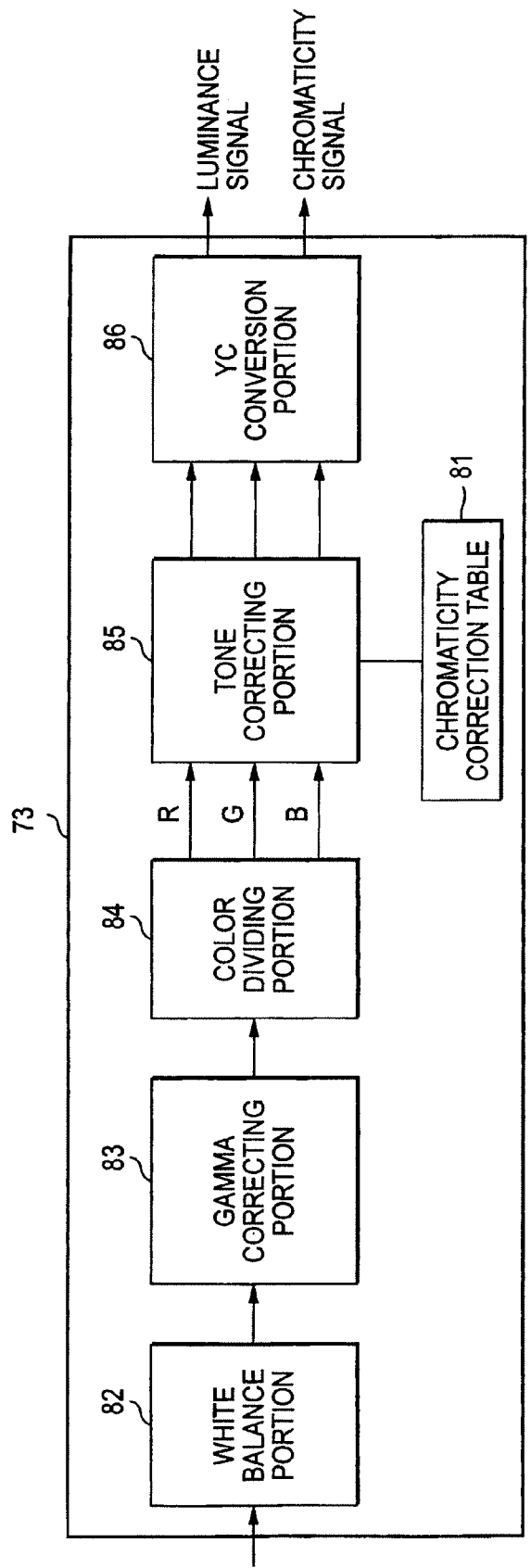
FIG. 4 is a block diagram showing a configuration of a detailed example of an image processing section.

FIG. 4 is a block diagram illustrating a configuration of a detailed example of the image processing section. The image processing section 73 includes a white balance portion 82, a gamma correction portion 83, a color dividing portion 84, a chromaticity correcting portion 85, and a YC conversion portion 86. The white balance portion 82 performs a white balance adjustment on the digital image signal output from the A/D converter 65, and gives the adjusted image data to the gamma correction portion 83. The gamma correction portion 83 performs a gamma correction on the input image data. The color dividing portion 84 creates the respective image signals of R (red), G (green), and B (blue) from the image data subjected to the gamma correction, and gives the image signal to the chromaticity correcting portion 85.

The chromaticity correcting portion 85 reads the correction data registered in the chromaticity correction table 81 to be described later in detail, and performs a correction process on the respective image signals of R, G, and B input from the color dividing portion 84 so as to obtain an image having correct chromaticity. The image signal subjected to the color correction process is converted into a color video signal of a luminance signal (Y) and a color difference signal (Cb and Cr) by the YC conversion section 86.

The video signal converted into the color video signal and output from the image processing section 73 is input to the control section 67, and is displayed on the display unit 15 in the form of an endoscope observation image together with a variety of information by the control section 67. If necessary, the video signal is stored in a storage section configured as a memory or a storage device.

Next, the individual information of the endoscope will be described.

As shown in FIG. 1, the endoscope characteristics storing section 75 is provided in the inside of the endoscope 11. The endoscope characteristics storing section 75 is configured as a non-volatile memory, and stores the individual information of the endoscope 11 in advance. Specifically, the light emission spectrum information and the excitation spectrum information as the original light emission characteristics information of the fluorescent body 57 actually provided in the endoscope 11 are stored in the endoscope characteristics storing section 75. In addition, the spectral characteristics information of the color filters of R, G, B (or C, M, Y or C, M, Y, G) of the imaging element 21 is also stored in the endoscope characteristics storing section 75. Here, the excitation spectrum information is information representing a distribution state for each wavelength involved with the energy absorption characteristics of the fluorescent body 57 with respect to the external light supplied for the excitation. In addition, the light emission spectrum information is information representing the spectral intensity of fluorescence actually generated from the fluorescent body 57 by the light supplied from the outside. Further, the spectral characteristics information is the information that represents the spectral sensitivity characteristics of the imaging element 21 depending on the spectral sensitivity of the color filter.

In fact, the light emission characteristics of the fluorescent body 57 are measured before the use of the endoscope, and the excitation spectrum information and the light emission spectrum information obtained from the result are stored in the endoscope characteristics storing section 75. Also, in the same way, the spectral characteristics information of the color filter is stored in the endoscope characteristics storing section 75. Furthermore, in addition to the measurement, the light emission characteristics may be the accurate characteristics information of the fluorescent body 57 which is prepared in advance may be stored in the endoscope characteristics storing section 75.

Figure 5:
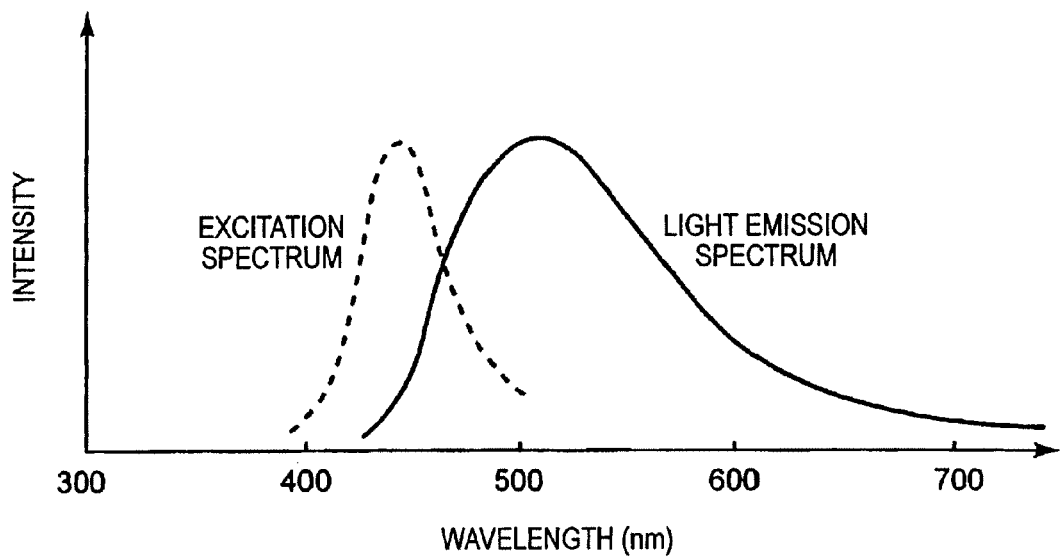
FIG. 5 is a graph showing an example of a light emission spectrum and an excitation spectrum involved with a particular fluorescent body.

Here, FIG. 5 shows an example of the excitation spectrum and the light emission spectrum of the particular fluorescent body 57. In the case of the fluorescent body 57 having the characteristics shown in FIG. 5, as seen from the curve of the excitation spectrum depicted by the dotted line, it is understood that the light within the wavelength bandwidth of about 420 to 470 nm is absorbed, and particularly, the light of the wavelength of about 445 nm is highly efficiently absorbed. The fluorescent body 57 is excited by the absorbed excitation light, and emits fluorescence of the spectrum shown in the light emission spectrum depicted by the solid line.

In addition, the light emission intensity of the fluorescent body 57 is changed in accordance with the magnitude of the absorbed energy. Like the excitation spectrum shown in FIG. 5, since the absorption characteristics of the excitation light of the fluorescent body 57 are changed in accordance with the wavelength, the light emission intensity of the fluorescent body 57 is changed in accordance with the wavelength of the light supplied from the outside.

Figure 6:
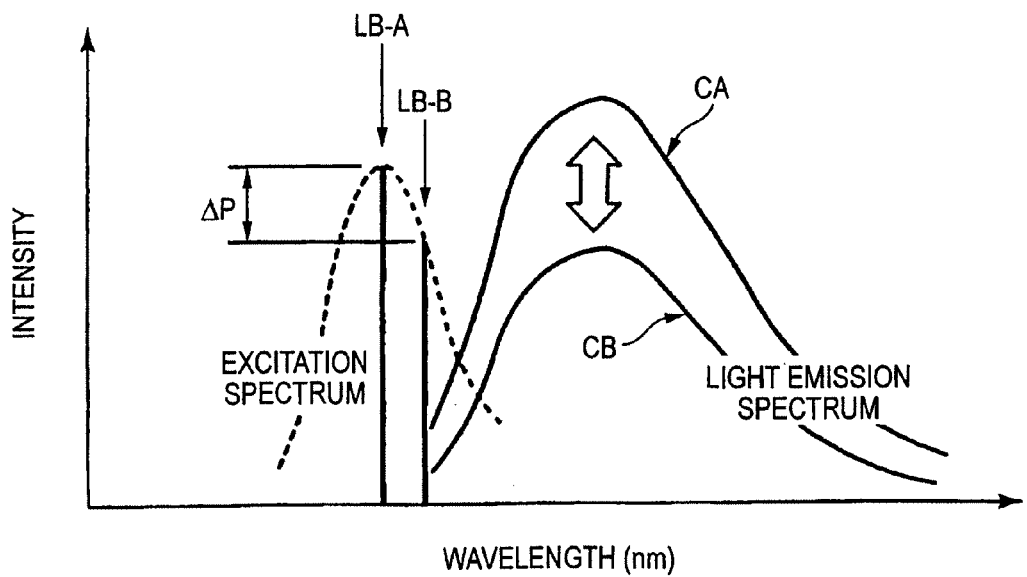
FIG. 6 is an explanatory diagram illustrating a variation in the light emission spectrum when there is an offset of the light emission wavelength of the blue laser light source.

For example, as shown in FIG. 6, if it is assumed that the light emission wavelength of the blue laser light source 47 is deviated, in the laser light LB-A of the stipulated wavelength of 445 nm, highly efficient absorption occurs at a wavelength at which the excitation spectrum substantially reaches peak. However, in the laser light of LB-B, since the light emission wavelength is deviated, the intensity of the excitation spectrum is decreased by ΔP. Then, in the laser light LB-B, the light emission intensity is the same as that of the laser light LB-A, and the light emission spectrum of the fluorescent body 57 is decreased from CA to CB, which causes a relative difference in the light emission intensity of the fluorescent body between the laser lights LB-A and LB-B.

Regarding the excitation spectrum information, the light emission spectrum information, and the spectral characteristics information stored in the endoscope characteristics storing section 75, when the information representing the curve of each of continuous spectrums of a plurality of wavelengths is stored as a table or a numerical equation, it is possible to predict more highly precisely the spectrum of the illumination light, and to correct highly precisely the chromaticity.

In addition, the individual information of the light source is as described below.

As shown in FIG. 1, the light source device 41 includes the light source information storing section 74. The light source information storing section 74 is configured as a non-volatile memory, and stores information representing the wavelength of the laser light output from the light source as the original light source information of the light source device 41. That is, the light source information storing section 74 stores information representing the central wavelength (the wavelength having the maximum intensity) of the laser light emitted from at least the blue laser light source 47. In addition, the information representing the central wavelength of the laser light emitted from the violet laser light source 45 may be also stored. The central wavelength information is stored in such a manner that the light emission characteristics of the laser light sources 45 and 47 of the light source device 41 are measured before using the endoscope, and the information obtained as a result thereof is stored in the light source information storing section 74. In addition to the measurement, the accurate characteristics information of each of the laser light sources 45 and 47 prepared in advance may be stored in the endoscope characteristics storing section 75.

Next, the procedure of correcting the chromaticity information of the captured image will be described with reference to FIG. 7.

Figure 7:
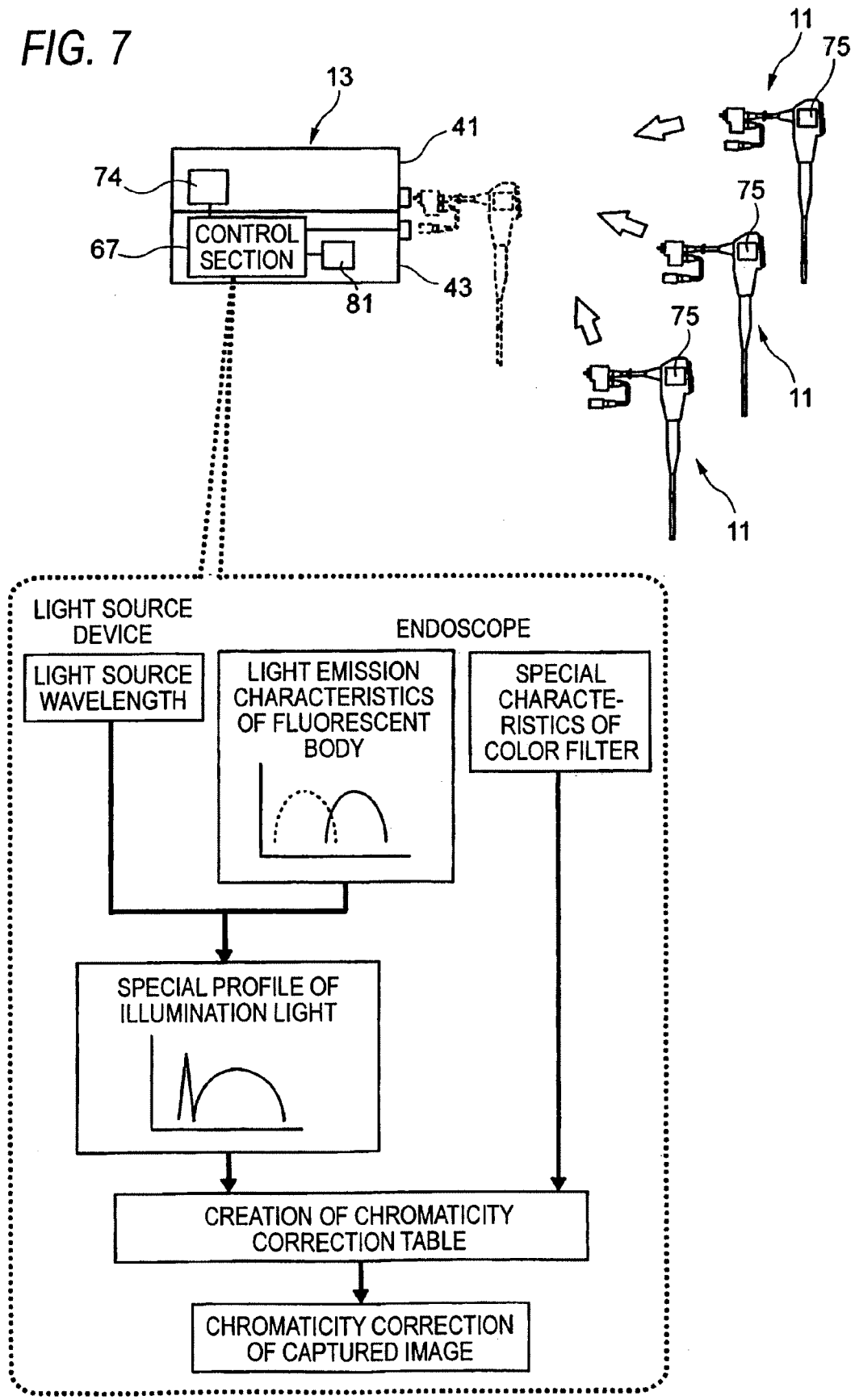
FIG. 7 is an explanatory diagram illustrating a procedure of correcting chromaticity information of a captured image.

As shown in FIG. 7, when any one of the endoscopes 11 is connected to the control device 13, the control section 67 of the processor 43 obtains the information on the light emission wavelength of the light source from the light source information storing section 74 of the light source device 41, and obtains the information of the fluorescent body light emission characteristics as the excitation spectrum information and the light emission spectrum information from the endoscope characteristics storing section 75 of the endoscope 11 connected to the control device 13. Then, the control section creates an illumination light spectral profile 76 of the illumination light emitted from the front end of the endoscope 11 on the basis of the information on the original parameters. That is, the control section obtains the intensity of the fluorescent body light emission spectrum from the light emission wavelength of the light source and the excitation spectrum of the fluorescent body, and obtains the illumination light spectral profile obtained by synthesizing the blue laser light with the fluorescent body light emission spectrum. In addition, the information may be obtained from the light source information storing section 74 before the endoscope 11 is connected to the control device.

Subsequently, the control device 13 creates information necessary for correctly reproducing the chromaticity of the corrected image on the basis of the contents of the illumination light spectral profile, and stores the information in the chromaticity correction table 81. That is, in order to obtain the output image having a chromaticity equal to that of the case where a predetermined standard light is used as the illumination light, the control device creates the chromaticity correction table 81 for subjecting the image signal to the chromaticity correction corresponding to a difference between the spectral characteristics (profile) of the standard light and the spectral characteristics of the actual illumination light, and stores the contents of the chromaticity correction table 81 in the correction information storing section 72 shown in FIG. 1.

Then, the image processing section 73 of the control device 13 corrects the imaging signal obtained from the endoscope 11 on the basis of the chromaticity correction table 81 by referring to the correction information storing section 72, and outputs the observation image having an appropriate chromaticity to the control section 67. With the above-described processes, the image captured by the endoscope 11 is output with an appropriate tone at all times regardless of the individual difference of the fluorescent body of the endoscope and the individual difference of the light source, and is displayed or stored as an image having a tone appropriate for the diagnosis.

Further, since the chromaticity correction table 81 is created by including the spectral characteristics of the color filter of the imaging element 21, it is possible to more accurately perform the chromaticity correction. That is, the filter layers corresponding to the reference colors of R, G, B or C, M, Y (or C, M, Y, G) are formed for each pixel in the light receiving surface of the imaging element 21, thereby detecting the luminance level of each reference color. However, an individual difference occurs in the spectral sensitivity characteristics for each imaging element due to a reason such as a variation in the material or thickness of the color filter. Even when there is an individual difference in the imaging element, if the information of the spectral characteristics of the color filter is known, the imaging signal may be adjusted to have a predetermined tone as a reference by using the information of the spectral characteristics. In this configuration example, the chromaticity correction table is created on the basis of the individual information of the light emission characteristics of the color filter of the imaging element in addition to the individual information of the spectral characteristics of the fluorescent body and the individual information of the light emission characteristics of the light source unit. Since the imaging signal is corrected on the basis of the chromaticity correction table, it is possible to output the captured image with a constant tone at all times regardless of the individual difference of the color filter of the imaging element 21.

As described above, the image processing section 73 functions as an illumination light spectrum calculating means for calculating the illumination light spectrum obtained by the illumination optical system on the basis of the individual information of the light emission characteristics of the fluorescent body 57 provided in the endoscope 11 connected to the control device 13 and the individual information of the light emission characteristics of each of the laser light sources 45 and 47, a chromaticity correction table creating means for creating the chromaticity correction table used to correct the chromaticity information of the imaging signal in accordance with the illumination light spectrum, and an image correcting means for correcting the imaging signal output from the imaging element 21 by using the created chromaticity correction table.

Further, although it is not shown in the drawings, a switch capable of detecting the connection state between the control device 13 and the endoscope 11 is provided around the connectors 25A and 25B used to connect the control device and the endoscope to each other, and the creation process of the illumination light spectral profile and the chromaticity correction table is automatically started by using a detection signal output from the switch when the endoscope 11 is connected to the control device as a trigger, whereby the control section 67 is capable of automatically updating the chromaticity correction table 81.

Next, the modified example of the configuration or the operation of the endoscope system will be described below.

Figure 8:
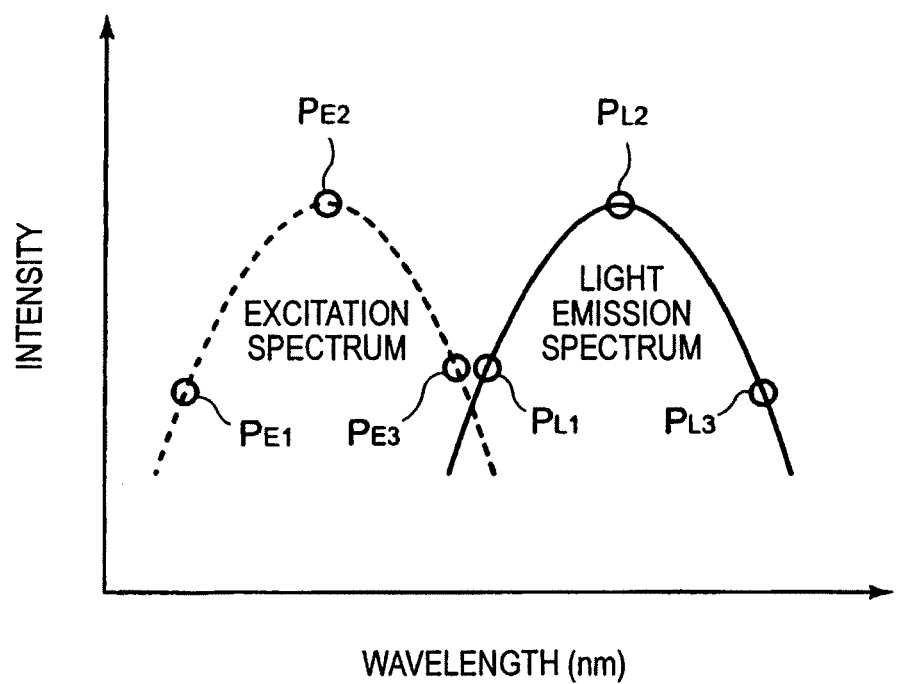
FIG. 8 is an explanatory diagram illustrating a method of decreasing a storage capacity of an endoscope characteristics storing section.

First, when the storage capacity of the endoscope characteristics storing section 75 of the endoscope 11 shown in FIG. 1 is limited, the amount of data of the information stored in the endoscope characteristics storing section 75 may be reduced. An example of reducing the amount of data is shown in FIG. 8. The substantial characteristics of the excitation spectrum curve may be understood by estimating only the information on at least three types of $P_{E1}$, $P_{E2}$, and $P_{E3}$ corresponding to different wavelengths of the maximum value and the approximate values thereof in the excitation spectrum. In addition, even in the light emission spectrum characteristics, the substantial characteristics of the light emission spectrum curve may be understood by estimating only the information on at least three types of $P_{L1}$, $P_{L2}$, and $P_{L3}$ corresponding to different wavelengths.

Therefore, the information for three points is stored as each of the excitation spectrum information and the light emission spectrum information. Accordingly, since the wavelengths other than three points are obtained by the estimation through the interpolation process based on a small amount of data, it is possible to perform the color correction process without largely degrading precision.

Figure 9:
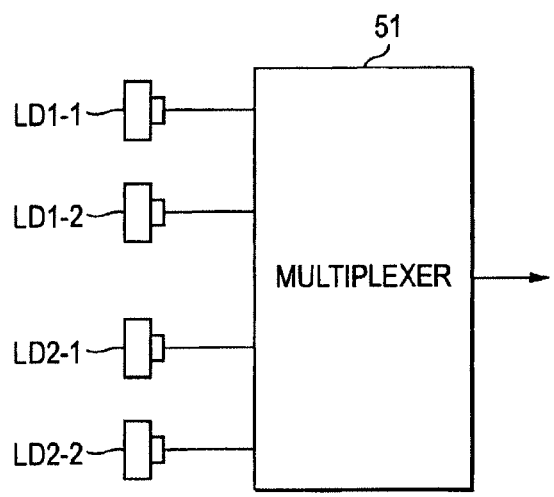
FIG. 9 is a block diagram showing a configuration of a part of the light source device of the first modified example.
Figure 10:
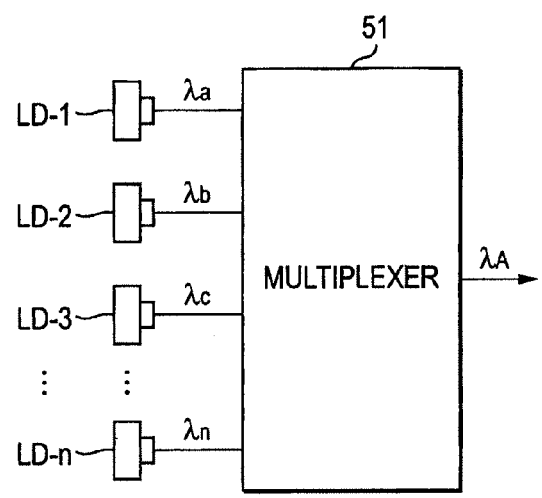
FIG. 10 is a block diagram showing a configuration of a part of the light source device of the second modified example.
Figure 11:
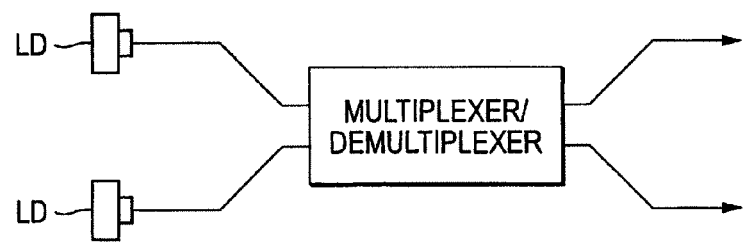
FIG. 11 is a block diagram showing a configuration of a part of the light source device using a multiplexer/demultiplexer.
Figure 12:
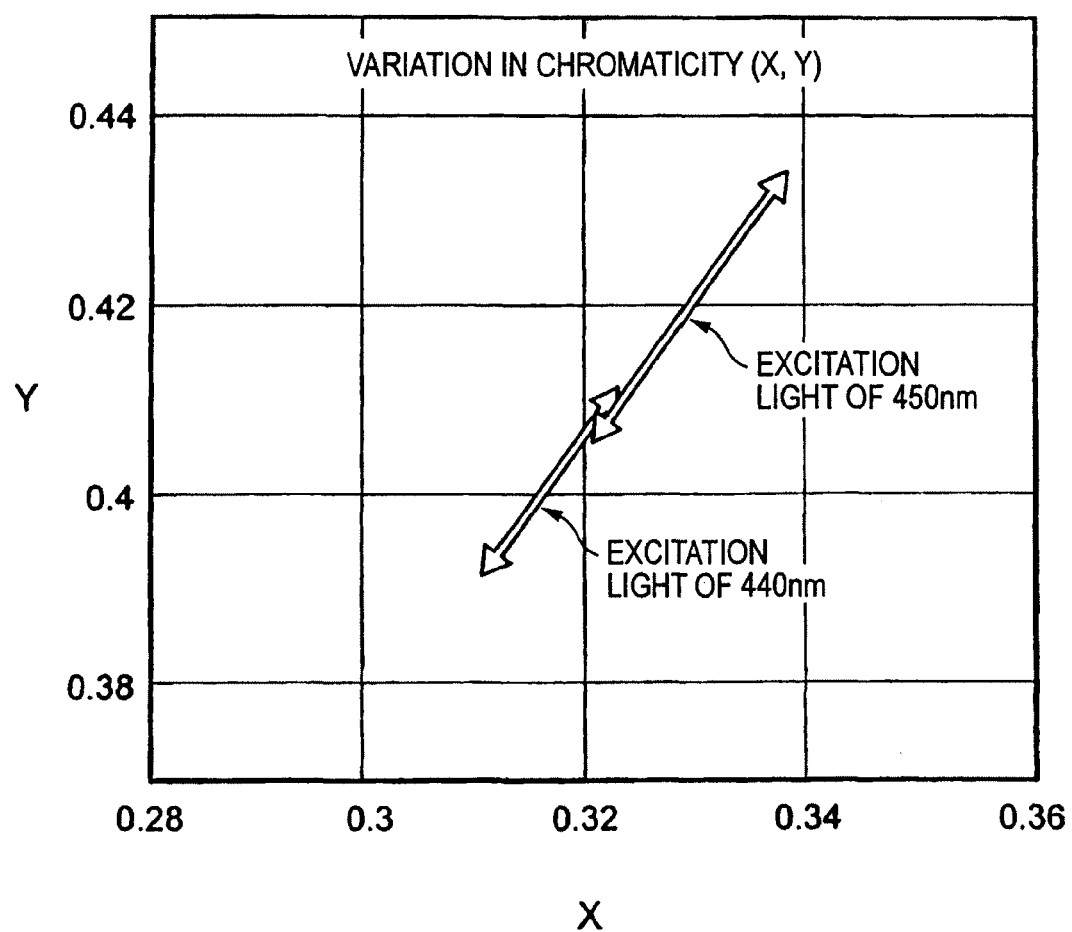
FIG. 12 is a chromaticity diagram showing a variation in the chromaticity of the illumination light of the endoscope.

Next, another modified example of the light source device 41 is shown in FIGS. 9 to 11.

In the first modified example shown in FIG. 9, two laser light sources LD1-1 and LD1-2 each having a central light emission wavelength of 445 nm and two laser light sources LD2-1 and LD2-2 each having a central light emission wavelength of 405 nm are provided in one light source device. Then, the lights emitted from the four laser light sources LD1-1, LD1-2, LD2-1, and LD2-2 are multiplexed by using the combiner 51.

In this case, since the lights emitted from plural types of laser light sources are multiplexed by using the laser light sources stipulated to have the same wavelength, it is possible to absorb a variation in the wavelength caused by the individual differences of the laser light sources, and to uniformize wavelength of the illumination light. For example, the stipulated light emission wavelengths of the laser light sources LD1-1 and LD1-2 are 405 nm. However, since the laser light sources actually have individual differences caused by a difference in the manufacturing environment, the lights may have a wavelength offset from the 405 nm by, for example, about ±5 nm. Therefore, as shown in FIG. 9, the differences of the wavelengths of the laser light sources are averaged by multiplexing the lights of the plurality of the laser light sources LD1-1 and LD1-2. As a result, a variation in the light emission wavelength caused by the individual differences may be further reduced in the wavelength of the multiplexed light than that of the case where the laser light sources each having different wavelengths (445 nm and 405 nm) are used.

In the same way, in the second modified example shown in FIG. 10, n number of laser light sources LD-1, LD-2, LD-3, and LD-n each stipulated to have the same light emission wavelength are provided in one light source device, and the lights emitted from the n number of laser light sources are multiplexed by using the combiner 51. That is, it is possible to further decrease a variation in the light emission wavelength caused by the individual differences as the number of laser light sources to be used increases.

Further, in the light multiplexing operation of the above-described modified examples, when a multiplexer/demultiplexer (fiber coupler) as a single component having both multiplexing and demultiplexing functions is used as shown in FIG. 11, the number of components is decreased, thereby further decreasing the size of the endoscope system.

While the endoscope system has been described, the endoscope system has a configuration in which plural types of laser light sources having different light emission wavelengths are mounted on the light source device 41, but may, of course, adopt a configuration in which only the laser light source for the white illumination light is mounted thereon. In addition, the combiner 51 or the coupler 53 may be appropriately omitted.

Further, the endoscope system adopts a configuration in which the individual information of the fluorescent body of the endoscope 11 is stored in the endoscope characteristics storing section 75 inside the endoscope 11, but may adopt a configuration in which the spectral characteristics information of the color filter or the light emission characteristics information of the fluorescent body are stored in the external storage means such as a server connected to the processor 43 together with the individual identification information of the endoscope 11, and the individual information for the endoscope 11 connected to the control device 13 is referred to from the external storage means through inquiry.

Furthermore, the combiner 51 or the coupler 53 shown in FIG. 1 may be configured as, for example, a dichroic mirror instead of the fiber coupler so as to perform the multiplexing/demultiplexing operation.

The present invention is not limited to the above-described embodiment, but corrections and applications thereof may be made by the person skilled in the art on the basis of the description of the specification and the known technology, and those are included in the scope required to be protected.

As described above, the present specification discloses the following items.

(1) According to an aspect of the invention, an endoscope system includes: an endoscope that includes an illumination optical system with a fluorescent body formed in an optical path and an imaging optical system with an imaging element outputting an imaging signal of an optical image; and a control device that includes a light source unit which supplies an excitation light to the illumination optical system so as to emit light from the fluorescent body and an image processing section which corrects the imaging signal output from the imaging element, wherein the image processing section includes: an illumination light spectrum calculating unit for calculating an illumination light spectrum obtained by the illumination optical system based on individual information of light emission characteristics of the fluorescent body provided in the endoscope connected to the control device and individual information of light emission characteristics of the light source unit; a chromaticity correction table creating unit for creating a chromaticity correction table to correct chromaticity information of the imaging signal in accordance with the illumination light spectrum; and an image correcting unit for correcting the imaging signal output from the imaging element by referring the created chromaticity correction table.

According to the endoscope system, even when the endoscope connected to the control device is exchanged, it is possible to calculate the spectrum of the actual illumination light on the basis of the individual information of the endoscope in use, and the light emission characteristics of the light source unit and the fluorescent body. Accordingly, since the chromaticity correction table is created on the basis of the spectrum of the illumination light, and the imaging signal is corrected on the basis of the chromaticity correction table, it is possible to reproduce the image information having a correct tone at all times.

(2) In the endoscope system of (1), the individual information of the light emission characteristics of the fluorescent body includes information of an excitation spectrum representing light absorbing characteristics of the fluorescent body and information of a light emission spectrum of the light excited by absorbed optical energy and emitted from the fluorescent body.

According to the endoscope system, since the individual information of the light emission characteristics of the fluorescent body includes the excitation spectrum and the light emission spectrum, it is possible to obtain the light emission spectrum for the light having an arbitrary wavelength.

(3) In the endoscope system of (2), the individual information of the light emission characteristics of the light source unit includes information of a light emission wavelength of the light source unit.

According to the endoscope system, since the individual information of the light emission characteristics of the light source unit includes the light emission wavelength of the light source unit, it is possible to accurately obtain the light emission spectrum of the fluorescent body.

(4) In the endoscope system of (1), the endoscope includes an endoscope characteristics storing section that stores individual information of the light emission characteristics of the fluorescent body.

According to the endoscope system, since the endoscope characteristics storing section of the endoscope connected to the control device is referred to, it is possible to simply obtain the light emission characteristics of the fluorescent body.

(5) The endoscope system of (4) may further include: a connection detecting unit for detecting whether the endoscope is connected to the control device, wherein the image processing section obtains the individual information of the light emission characteristics of the fluorescent body from the endoscope characteristics storing section of the endoscope connected to the control device based on a trigger of detecting that the endoscope switches from a non-connection state to a connection state, and creates the chromaticity correction table.

According to the endoscope system, when the endoscope connected to the control device is exchanged with another one, the chromaticity correction table is automatically created in accordance with the original characteristics of the newly connected endoscope. Accordingly, even when a particular operation is not performed by the operator upon exchanging the endoscope, the image is automatically corrected in accordance with the characteristics of the endoscope.

(6) In the endoscope system of (1), the control device includes a light source information storing section that stores the individual information of the light emission characteristics of the light source unit.

According to the endoscope system, since the control device refers to the light source information storing section, it is possible to simply obtain the central light emission wavelength of the light source unit in use.

(7) In the endoscope system of (1), the light source unit includes a semiconductor light emitting element as a light emitting source.

According to the endoscope system, it is possible to obtain the illumination light having high luminance by improving the light emission efficiency.

(8) In the endoscope system of (7), the light source unit includes a multiplexer unit for multiplexing the lights emitted from a plurality of the semiconductor light emitting elements and supplying the multiplexed light to the illumination optical system of the endoscope.

According to the endoscope system, even when the semiconductor light emitting element having a variation in the light emission wavelength caused by the individual differences is used, since the lights emitted from the plurality of semiconductor light emitting elements are multiplexed, a variation in wavelength is reduced, and a variation in the illumination light spectrum caused by the individual differences of the light source units becomes small.

(9) In the endoscope system of (8), wherein the endoscope includes a plurality of pairs each including the fluorescent body and a light guiding path disposed in the fluorescent body so as to face a light emission end, and wherein the light source unit includes a demultiplexer unit for demultiplexing and supplying the multiplexed light to each of the light guiding paths.

According to the endoscope system, since it is possible to uniformly guide the light having a reduced variation in wavelength by multiplexing to the fluorescent bodies, it is possible to emit uniform illumination light from the fluorescent bodies.

(10) In the endoscope system of (9), the multiplexer unit and the demultiplexer unit are configured as a single fiber coupler.

According to the endoscope system, it is possible to decrease the size of the light source unit, and to decrease the number of components.

(11) In the endoscope system of (9), each of the multiplexer unit and the demultiplexer unit is configured as a dichroic mirror.

According to the endoscope system, it is possible to configure the light source unit at low cost by using a simple element.

(12) In the endoscope system of (1), the image processing section creates the chromaticity correction table based on individual information of spectral characteristics of a color filter of the imaging element in addition to the individual information of the light emission characteristics of the fluorescent body and the individual information of the light emission characteristics of the light source unit.

According to the endoscope system, even when there are individual differences in the spectral characteristics of the color filters of the imaging element, it is possible to reproduce the image information having a correct tone at all times by correcting the individual differences.

(13) In the endoscope system of (12), the endoscope includes an endoscope characteristics storing section that stores the individual information of the light emission characteristics of the fluorescent body and the individual information of the spectral characteristics of the color filter of the imaging element.

According to the endoscope system, since the endoscope characteristics storing section of the endoscope connected to the control device is referred to, it is possible to simply obtain the spectral characteristics of the color filter of the imaging element.

What is claimed is:

1. A endoscope system comprising:
an endoscope that includes an illumination optical system with a fluorescent body formed in an optical path and an imaging optical system with an imaging element outputting an imaging signal of an optical image;
and a control device that includes a light source unit which supplies an excitation light to the illumination optical system so as to emit light from the fluorescent body and an image processing section which corrects the imaging signal output from the imaging element, wherein the image processing section includes:
an illumination light spectrum calculating unit for calculating an illumination light spectrum obtained by the illumination optical system based on individual information of light emission characteristics of the fluorescent body provided in the endoscope connected to the control device and individual information of light emission characteristics of the light source unit;
a chromaticity correction table creating unit for creating a chromaticity correction table to correct chromaticity information of the imaging signal based on a difference between the spectral characteristics profile of the standard light and the spectral characteristics of the actual illumination light;
and an image correcting unit for correcting the imaging signal output from the imaging element by referring the created chromaticity correction table.

2. The endoscope system according to claim 1, wherein the individual information of the light emission characteristics of the fluorescent body includes information of an excitation spectrum representing light absorbing characteristics of the fluorescent body and information of a light emission spectrum of the light excited by absorbed optical energy and emitted from the fluorescent body.

3. The endoscope system according to claim 2, wherein the individual information of the light emission characteristics of the light source unit includes information of a light emission wavelength of the light source unit.

4. The endoscope system according to claim 1, wherein the endoscope includes an endoscope characteristics storing section that stores individual information of the light emission characteristics of the fluorescent body.

5. The endoscope system according to claim 4, further comprising:
a connection detecting unit for detecting whether the endoscope is connected to the control device,
wherein the image processing section obtains the individual information of the light emission characteristics of the fluorescent body from the endoscope characteristics storing section of the endoscope connected to the control device based on a trigger of detecting that the endoscope switches from a non-connection state to a connection state, and creates the chromaticity correction table.

6. The endoscope system according to claim 1, wherein the control device includes a light source information storing section that stores the individual information of the light emission characteristics of the light source unit.

7. The endoscope system according to claim 1, wherein the light source unit includes a semiconductor light emitting element as a light emitting source.

8. The endoscope system according to claim 7, wherein the light source unit includes a multiplexer unit for multiplexing the lights emitted from a plurality of the semiconductor light emitting elements and supplying the multiplexed light to the illumination optical system of the endoscope.

9. The endoscope system according to claim 8,
wherein the endoscope includes a plurality of illumination ports, an illumination port of the plurality of illumination ports including the fluorescent body, and a plurality of light guiding paths disposed in the fluorescent body so as to face a light emission end, and
wherein the light source unit includes a demultiplexer unit for demultiplexing and supplying the multiplexed light to a light guiding path of the plurality of light guiding paths.

10. The endoscope system according to claim 9, wherein the multiplexer unit and the demultiplexer unit are configured as a single fiber coupler.

11. The endoscope system according to claim 9, wherein each of the multiplexer unit and the demultiplexer unit is configured as a dichroic mirror.

12. The endoscope system according to claim 1, wherein the image processing section creates the chromaticity correction table based on individual information of spectral characteristics of a color filter of the imaging element in addition to the individual information of the light emission characteristics of the fluorescent body and the individual information of the light emission characteristics of the light source unit.

13. The endoscope system according to claim 12, wherein the endoscope includes an endoscope characteristics storing section that stores the individual information of the light emission characteristics of the fluorescent body and the individual information of the spectral characteristics of the color filter of the imaging element.

14. The endoscope system according to claim 1, wherein the control device creates the chromaticity correction table that subjects the imaging signal to the chromaticity correction table corresponding to a difference between a spectral characteristic of standard light and a spectral characteristic of actual illumination light.

* * * * *